(12) United States Patent
Santagostino et al.

(10) Patent No.: US 7,423,146 B2
(45) Date of Patent: Sep. 9, 2008

(54) PROCESS FOR THE MANUFACTURING OF PHARMACEUTICALLY ACTIVE 3,1-BENZOXAZINE-2-ONES

(75) Inventors: Marco Santagostino, Mittelbiberach (DE); Werner Rall, Mittelbiberach (DE); Rainer Soyka, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/586,237

(22) Filed: Oct. 25, 2006

(65) Prior Publication Data

US 2007/0112191 A1 May 17, 2007

(30) Foreign Application Priority Data

Nov. 9, 2005 (EP) .................. 05110502

(51) Int. Cl.
*C07D 265/18* (2006.01)
(52) U.S. Cl. .......................... 544/71; 544/92
(58) Field of Classification Search ............. 544/71, 544/92

See application file for complete search history.

(56) References Cited

U.S. PATENT DOCUMENTS 4,341,778 A * 7/1982 Mentrup et al. .......... 514/229.8

(Continued)

FOREIGN PATENT DOCUMENTS

CA 1 165 317 A 4/1984

(Continued)

OTHER PUBLICATIONS

E.J. Corey; Reduction of Carbonyl Compounds with Chiral Oxazaborolidine Catalysts: A New Paradigm for Enantioselective Catalysis and a Powerful New Synthetic Method; Angew. Chem. Int. Ed, 1998, vol. 37 pp. 1986-2012.

(Continued)

*Primary Examiner*—Peter O'Sullivan
(74) *Attorney, Agent, or Firm*—Michael P. Morris; Edouard G. Lebel; Timothy X. Witkowski

(57) ABSTRACT

A process for making a compound of formula 1

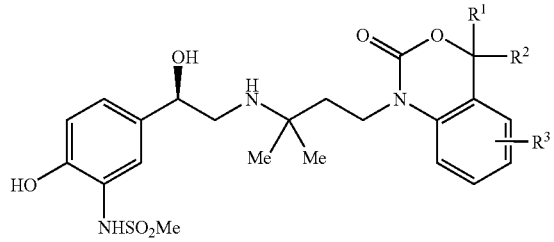

or a salt thereof, wherein:
$R^1$ and $R^2$ are each independently H, halogen, or $C_{1-4}$-alkyl, or $R^1$ and $R^2$ together are $C_{1-6}$-alkylene; and
$R^3$ is H, halogen, OH, $C_{1-4}$-alkyl, or O—$C_{1-4}$-alkyl, the process comprising:

(a) reacting a compound of formula 6

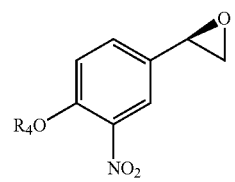

wherein $R^4$ is benzyl, diphenylmethyl, or trityl, each optionally substituted at, if available, an aryl group or an aliphatic carbon atom, with a compound of formula 7

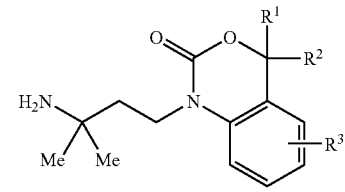

or a salt thereof, to obtain a compound of formula 5, or a salt thereof

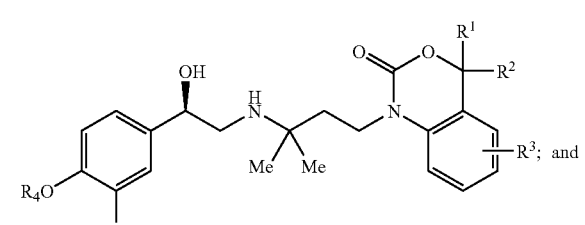

(b) reducing the nitro group of the compound of formula 5 to an amine group and mesylating this amine group and cleaving the protecting group during the reduction step or after the mesylation step to obtain the compound of formula 1.

21 Claims, No Drawings

U.S. PATENT DOCUMENTS

| | | | |
|---|---|---|---|
| 4,460,581 | A | 7/1984 | Schromm et al. |
| 4,570,630 | A | 2/1986 | Elliott et al. |
| 4,950,767 | A | 8/1990 | Kraatz |
| 7,220,742 | B2 | 5/2007 | Lustenberger et al. |
| 2006/0189605 | A1 | 8/2006 | Konctzki et al. |
| 2007/0027148 | A1 | 2/2007 | Lustenberger et al. |
| 2007/0066607 | A1 | 3/2007 | Fairhurst et al. |
| 2007/0112191 | A1 | 5/2007 | Santagostino et al. |
| 2008/0051392 | A1 | 2/2008 | Konetzki et al. |
| 2008/0053430 | A1 | 3/2008 | Nowak et al. |

FOREIGN PATENT DOCUMENTS

| | | |
|---|---|---|
| CA | 2 164 222 C | 12/1994 |
| CA | 2 232 151 C | 4/1997 |
| CA | 2 233 981 C | 4/1997 |
| CA | 2 237 853 C | 6/1997 |
| CA | 2 300 908 A1 | 4/1999 |
| CA | 2 450 961 A1 | 1/2003 |
| CA | 2 425 539 A1 | 4/2003 |
| CA | 2 425 560 A1 | 4/2003 |
| CA | 2 471 578 A1 | 8/2003 |
| CA | 2 472 149 A1 | 8/2003 |
| CA | 2 474 874 A1 | 8/2003 |
| CA | 2 552 784 A1 | 8/2005 |
| CA | 2 562 859 A1 | 11/2005 |
| DE | 36 09 152 A1 | 9/1987 |
| EP | 0 043 940 A1 | 1/1982 |
| EP | 0 237 507 A1 | 9/1987 |
| WO | 91/14468 A1 | 10/1991 |
| WO | 94/07607 A1 | 4/1994 |
| WO | 94/28958 A1 | 12/1994 |
| WO | 95/32937 A1 | 12/1995 |
| WO | 97/12683 A1 | 4/1997 |
| WO | 97/12687 A1 | 4/1997 |
| WO | 97/20590 A1 | 6/1997 |
| WO | 99/16530 A1 | 4/1999 |
| WO | 02/30928 A1 | 4/2002 |
| WO | 02/32898 A2 | 4/2002 |
| WO | 03/000265 A1 | 1/2003 |
| WO | 03/064417 A1 | 8/2003 |
| WO | 03/064418 A1 | 8/2003 |
| WO | 03/064419 A1 | 8/2003 |
| WO | 2004/087142 A1 | 10/2004 |
| WO | 2005/070908 A1 | 8/2005 |
| WO | 2005/111005 A1 | 11/2005 |
| WO | 2006/089859 A1 | 8/2006 |

OTHER PUBLICATIONS

Y.Hong; cis-1-Amino-2-indanol in Asymmetric Synthesis, Part 1. A Practical Catalyst System for the Enantioselective Borane Reduction of Aromatic Ketones; Tetrahedron Lett., 1994, vol. 35, NO. 36 pp. 6631-6634; Great Britain.

S. Itsuno; Asymmetric Reduction of Aliphatic Ketones with the Reagent Prepared from (S)-(-)-2-Amino-3methyl-1-1,1-diphenylbutan-1-ol and Borane; J. Org. Chem (1984) vol. 49 pp. 555-557.

G.J. Quallich; Diphenyloxazaborolidine A New Catalyst for Enantioselective Reduction of Ketones;Tetrahedron Lett (1993) vol. 34 No. 26 pp. 4145-4148; Great Britain.

S. Itsuno; Asymmetric Synthesis Using Chirally Modified Borohydrides, Part 1. Enantioselective Reduction of Aromatic Ketones with the Reagent Prepared from Borane and (S)-Valinol; J. Chem. Soc. Perkin Trans. I (1983) pp. 1673-1676.

R. Hett et al; Conformational Toolbox of Oxazaborolidine Catalysts in the Enantioselective Reduction of a-Bromo-Ketone for the Synthesis of (R,R)-Formoterol;Tetrahedron Letters (1998) vol. 39 pp. 1705-1708.

A. Hirao; Asymmetric Reduction of Aromatic Ketones with Chiral Alkoxy-amine-borane Complexes; J. Chem. Soc. Chem.Comm (1981) pp. 315-317.

G. J. Quallich; In Situ Oxazaborolidines, Practical Enantioselective Hydride Reagents;Synlett, DEc. 1993, p. 929.

M. Masui; A Practical Method for Asymmetric Borane Reduction of Prochiral Ketones Using Chiral Amino Alcohols and Trimethyl Borate; Synlett, Mar. 1997, pp. 273-274.

T. Hamada; Practical Synthesis of Optically Active Styrene Oxides via Reductive Transformation of 2-chloroacetophenones with Chiral Rhodium Catalysts; Org. Lett (2002) vol. 4 NO. 24 pp. 4373-4376.

J. Chandrasekharan; The Reduction of Oximes by Lithium Aluminum Hydride in Hexamethylphosphoramide Solvent; J. Org. Chem (1985) vol. 50 pp. 5448-5450.

J.S. Lodaya; Direct a-Mesyloxylation of Ketones and b-dicarbonyl Compounds with [Hydroxy(mesyloxy)iodo] benzene; J. Org. Chem (1988) vol. 53 p. 210.

K.Yutaka; 2-Amino-4-phenylthiazole derivatives as anti-atherogenic agents; Eur. J. Med. Chem. Chim.Ther (1981) vol. 16 pp. 355-362.

S. Kajigaeshi; z-Chloroination of Aromatic Acetyl Derivatives with Benzyltrimethylammonium Dichloroiodate; Synthesis Jul. 1988, vol. 7, pp. 545-546.

E. Vedejs; A Tyrosine-Derived Benzofuranone Related to a Diazonamide A; Org. Lett (2000) vol. 2 No. 8 pp. 1031-1032.

A. Guy; Selective a-Chloroination of Aryl Ketones; Synthesis 1982, 12, pp. 1018-1020.

A. V. Rama Rao et al; Enantioselective Catalytic reductions of Ketones with New Four Membered Oxazaborolidines: Application to (S)- Tetramisole; Tetrahedron: Asymmetry (1992) vol. 3 NO. 7 pp. 859-862; Elsevier Science Publisher.

Gerald F. Koser et al; One-Step Alpha-Tosyloxylation of Ketones with [Hydeoxy(tosyloxy)iodo]Benzene; Journal of Organic Chemistry (1982) vol. 47 No. 12 pp. 2487-2489.

Jonathan D. Bloom et al; Disodium (R,R0-5[2-[[2-(3Chlorophenyl)-2-hydroxyethyl]-amino]propyl]-1,3-benzodloxole-2,2-dicarboxylate (CL 316,243). A Potent Beta-Adrenergic Agonist Virtually Specific for Beta2 Receptors. A Promising Antidiabetic and Antiobesity Agent; Journal of medicinal Chemistry (1992) vol. 35 No. 16 pp. 3081-3084.

International Search Report and Written Opinion for corresponding international application PCT/EP2006/068157 mailed on Apr. 16, 2007.

Paula Yurkanis Bruice; Glossary: Organic Chemistry (1995) p. G-7.

International Search Report for PCT/EP2006/060033 mailed on May 4, 2006.

International Search Report for PCT/EP2007/058653 mailed Oct. 29, 2007.

International Search Report for PCT/EP2007/058654 mailed Dec. 6, 2007.

International Search Report for PCT/EP2007/058655 mailed Oct. 29, 2007.

* cited by examiner

PROCESS FOR THE MANUFACTURING OF PHARMACEUTICALLY ACTIVE 3,1-BENZOXAZINE-2-ONES

RELATED APPLICATION

This application claims priority to European Application No. 05110502.1, filed on Nov. 9, 2005, which is hereby incorporated by reference.

FIELD OF THE INVENTION

Betamimetics (β-adrenergic substances) are known from the prior art. Reference may be made, for example, to the disclosures of U.S. Pat. No. 4,460,581 or EP 43940, which proposes betamimetics for the treatment of a variety of complaints.

For drug treatment of diseases it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the well-being of the patient to a high degree.

It is particularly desirable to prepare a pharmaceutical composition which can be used therapeutically by administration once a day (single dose). The use of a drug once a day has the advantage that the patient can become accustomed relatively quickly to taking the drug regularly at certain times of the day.

The aim of the present invention is therefore to provide a process for the manufacturing of betamimetics which have a therapeutic benefit in the treatment of COPD and are characterized by a longer duration of activity and can thus be used to prepare pharmaceutical compositions with a longer duration of activity. A particular aim of the invention is to prepare betamimetics which, by virtue of their long-lasting effect, can be used to prepare a drug for administration once a day for treating COPD.

BRIEF DESCRIPTION OF THE INVENTION

The invention relates to a process for the manufacturing of organic compounds useful for treatment and prevention of respiratory diseases of general formula 1

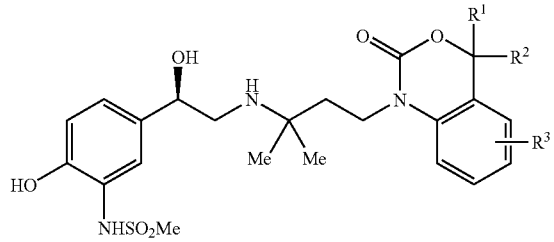

1 and pharmaceutically acceptable salts thereof, wherein:
$R^1$ and $R^2$ each independently mean H, halogen, or $C_{1-4}$-alkyl, or $R^1$ and $R^2$ are together have the meaning of $C_{1-6}$-alkylene; and
$R^3$ denotes H, halogen, OH, $C_{1-4}$-alkyl, or $O-C_{1-4}$-alkyl.

This invention further relates to optically pure intermediates for the synthesis of 1 and a process for their preparation. Accordingly, the invention relates in one aspect to a process for preparing compounds of formula 1 deprotecting compounds of formula 2

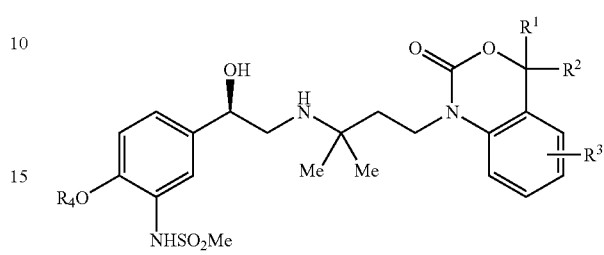

2 and salts thereof, wherein $R^1$, $R^2$, and $R^3$ are defined as above and $R^4$ is selected from a is group consisting of benzyl, diphenylmethyl, or trityl, each optionally substituted at, if available, an aryl group or an aliphatic carbon atom.

Alternatively, compounds of formula 1 are obtained by mesylation of compounds of formula 3

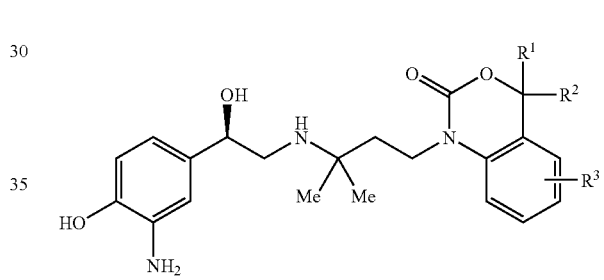

3

Compounds 2 can be prepared upon mesylation of compounds 4. In turn, compounds 4 are prepared by reducing compounds of formula 5

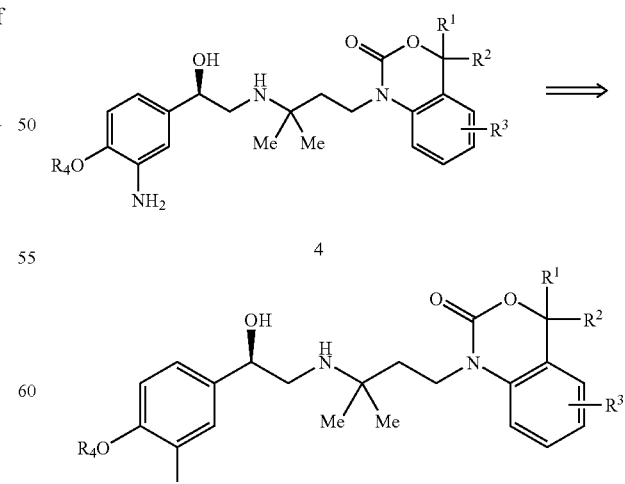

4

5 and compounds 3 are obtained by reduction of compounds 5. Compounds 5 are prepared by reacting optically pure compounds of formula 6

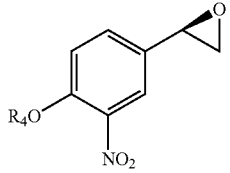
6 wherein $R^4$ has the above given meaning, with compounds of formula 7

7

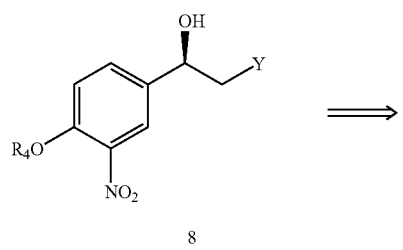

or a salt thereof, wherein $R^1$, $R^2$, and $R^3$ have the above given meaning. In another aspect, the present invention provides optically pure compounds of formula 8, and a process for their preparation which comprises asymmetric reduction of compounds of formula 9, in turn obtained from compounds 10

8

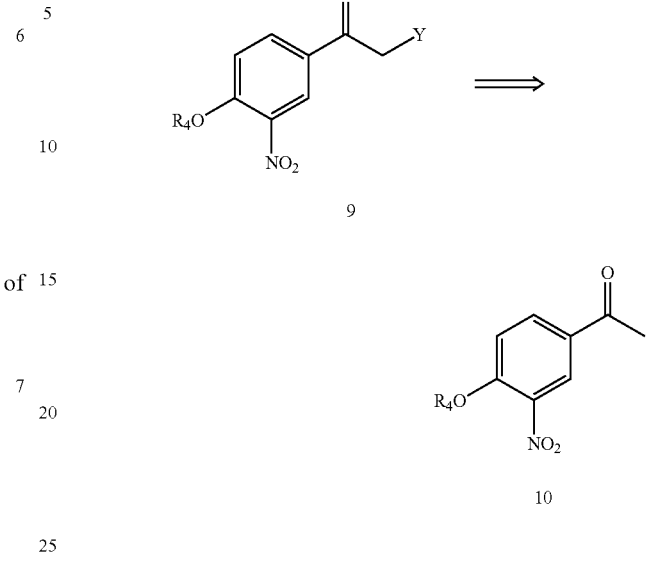

where $R^4$ is a hydroxy-protecting group as hereinbefore described, and Y is a chlorine or a sulfonyloxy based leaving group. Suitable examples include mesyloxy, tosyloxy, benzensulfonyl, or trifluoromethanesulfonyloxy.

DETAILED DESCRIPTION OF THE INVENTION

In one aspect the present invention relates to a practical and efficient process for the preparation of organic compounds of formula 1 as optically pure isomers. This method is particularly advantageous because it utilizes precursors of high crystallinity and enantiomeric purity that are readily obtained by asymmetric reduction techniques of readily available starting materials. The stereochemical integrity is maintained in the subsequent steps of the synthesis, which comprises crystalline or otherwise easily isolable intermediates and proceeds as illustrated in Scheme 1.

Scheme 1

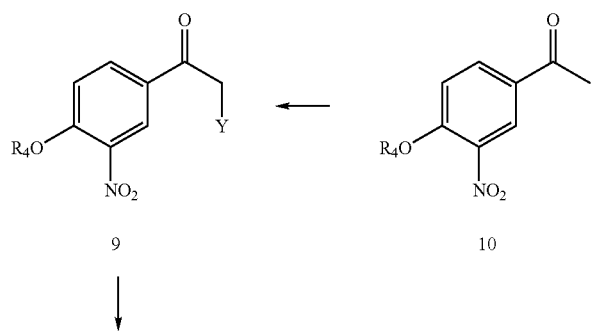

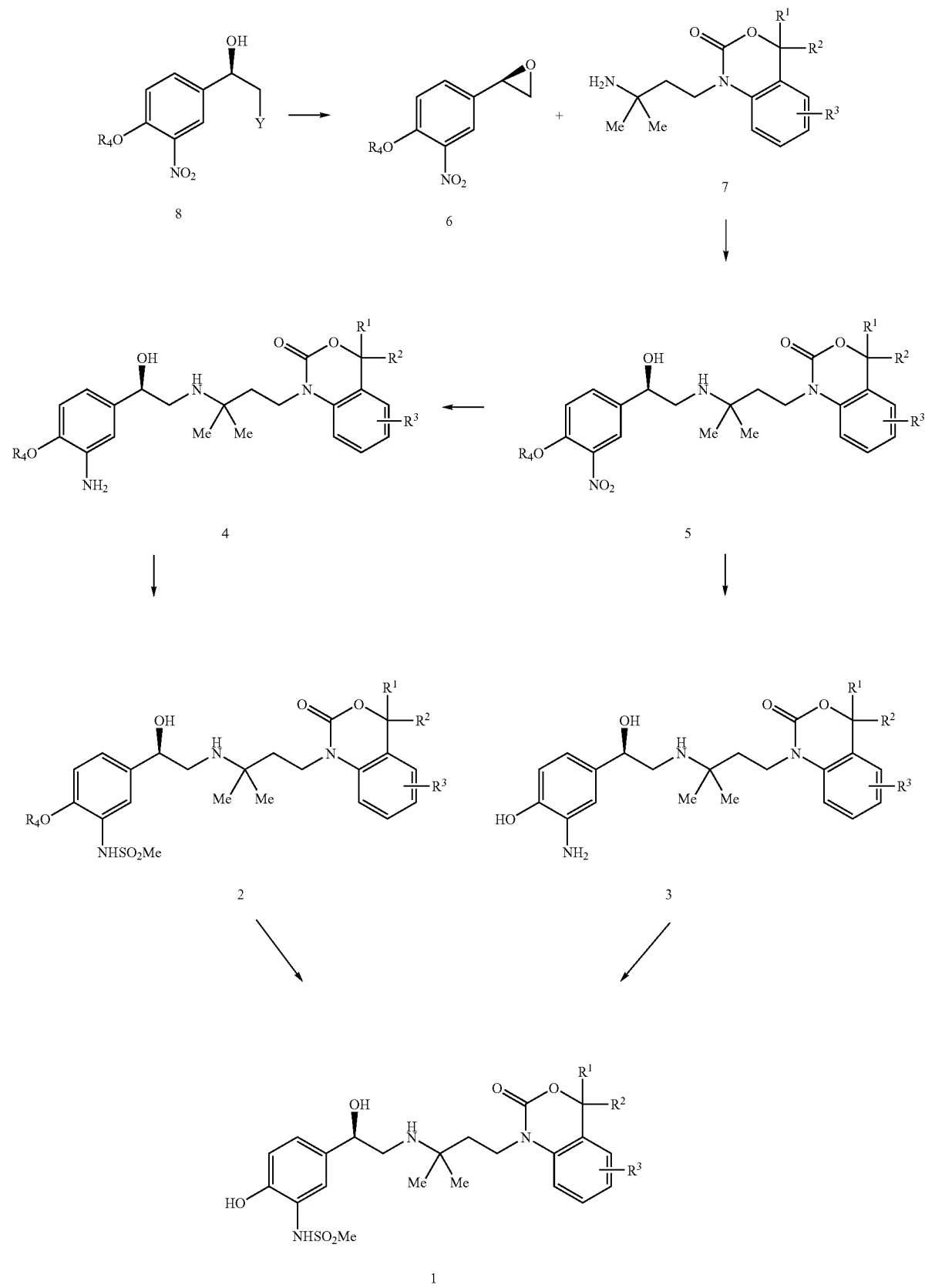

Therefore the invention relates to a process for manufacturing compounds of formula 1

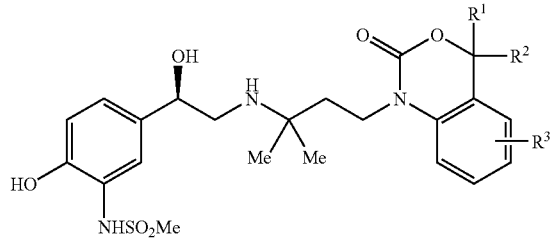

or a salt thereof, wherein:
R$^1$ and R$^2$ each independently mean H, halogen, or C$_{1-4}$-alkyl, or R$^1$ and R$^2$ are together have the meaning of C$_{1-6}$-alkylene; and
R$^3$ denotes H, halogen, OH, C$_{1-4}$-alkyl, or O—C$_{1-4}$-alkyl, characterized in that, a compound of formula 6

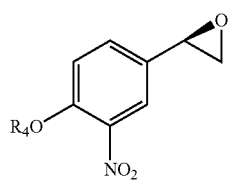

wherein R$^4$ is selected form the group consisting of benzyl, diphenylmethyl, or trityl, each optionally substituted at, if available, an aryl group or an aliphatic carbon atom is reacted with a compound of formula 7

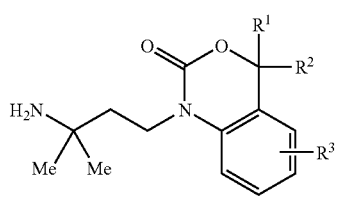

or a salt thereof, wherein R$^1$, R$^2$, and R$^3$ have the above given meaning, to a compound of formula 5, or a salt thereof

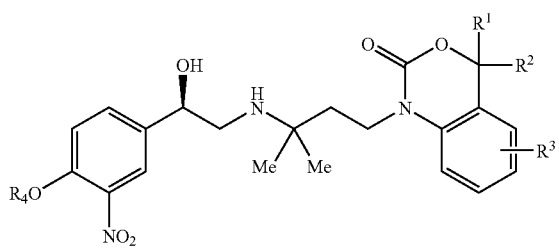

whereas compounds of formula 1 are obtained by reduction of the nitro group to an amine group, mesylation of this amine group and cleavage of the protecting group during the reduction step or after the mesylation step.

Preferred is a process wherein:
R$^1$ and R$^2$ each independently mean H, F, Cl, methyl, ethyl, propyl, or butyl, or R$^1$ and R$^2$ are together have the meaning of ethylene, propylene, butylene, or pentylene;
R$^3$ denotes H, F, Cl, OH, methyl, ethyl, methoxy, or ethoxy; and
R$^4$ is selected form the group consisting of benzyl or diphenylmethyl, each optionally substituted at if available an aryl group or an aliphatic carbon atom, with a group selected form F, Cl, Br, Me, Et, OMe, OEt, or O—$^i$Pr.

Particularly preferred is a process wherein:
R$^1$ and R$^2$ each independently mean H, methyl, ethyl, propyl, or R$^1$ and R$^2$ are together have the meaning of ethylene, propylene, butylene, or pentylene;
R$^3$ denotes H, F, OH, methyl, or methoxy; and
R$^4$ denotes benzyl optionally substituted at the aryl group or the aliphatic carbon atom with a group selected form F, Cl, Br, Me, Et, OMe, OEt, or O—$^i$Pr.

Particularly preferred are processes for manufacturing compounds of formula 1a-1h:

1a: N-(5-{2-[1,1-Dimethyl-3-(2-oxo-4,4-dipropyl-4H-benzo[d][1,3]oxazin-1-yl)propylamino]-1-hydroxyethyl}-2-hydroxyphenyl)methanesulfonamide 1b: N-[5-(2-{1,1-Dimethyl-3-[spiro(cyclohexan-1,4'-2H-3', 1'-benzoxazin)-2'-oxo-1-yl]-propylamino}-1-hydroxyethyl)-2-hydroxyphenyl]methanesulfonamide 1c: N-[5-(2-{1,1-Dimethyl-3-[spiro(cyclopropyl-1,4'-2H-3', 1'-benzoxazin)-2'-oxo-1yl]-propylamino}-1-hydroxyethyl)-2-hydroxyphenyl]methanesulfonamide 1d: N-(5-{2-[3-(4,4-Diethyl-2-oxo-4H-benzo[d][1,3]oxazin-1-yl)-1,1-dimethyl-propylamino]-1-hydroxyethyl}-2-hydroxyphenyl)methanesulfonamide 1e: N-(5-{2-[3-(4,4-Diethyl-6-fluoro-2-oxo-4H-benzo[d][1,3]oxazin-1-yl)-1,1-dimethyl-propylamino]-1-hydroxyethyl}-2-hydroxyphenyl)methanesulfonamide 1f: N-(5-{2-[3-(4,4-Diethyl-7-fluoro-2-oxo-4H-benzo[d][1,3]oxazin-1-yl)-1,1-dimethyl-propylamino]-1-hydroxyethyl}-2-hydroxyphenyl)methanesulfonamide 1g: N-(5-{2-[3-(4,4-Diethyl-8-methoxy-2-oxo-4H-benzo[d][1,3]oxazin-1-yl)-1,1-dimethyl-propylamino]-1-hydroxyethyl}-2-hydroxyphenyl)methanesulfonamide 1h: N-(5-{2-[3-(4,4-Diethyl-6-methoxy-2-oxo4H-benzo[d][1,3]oxazin-1-yl)-1,1-dimethyl-propylamino]-1-hydroxyethyl }-2-hydroxyphenyl)methanesulfonamide Preferred is a process wherein a compound of formula 6 is reacted with a compound of formula 7 in the presence of a suitable solvent. Preferred are organic solvents, especially preferred are suitable solvents selected form the group consisting of alcohols, ketones, aldehydes, ethers, or aromatic solvents, particularly preferred are ethanol, propanol, butanol, and tetrahydrofuran, or mixtures thereof.

The reacted stoichiometric ratio of compounds 6 and 7 is preferably between 1:1 and 1:5, particular preferred are ratios from 1:1; 1:1.05; 1:1.1; 1:1.15; 1:1.2; and 1:1.25.

The reaction is preferably conducted at increased temperatures, preferably above 40° C., more preferably above 60° C., most preferred at reflux of the solvent or of the solvents mixture with or without continuous removal of the solvent The preferred reaction time is between 1 hour and 48 hours, more preferably 3 hours and 24 hours, in particular 5 hours and 8 hours.

After the coupling reaction, the product of formula 5 is isolated directly from the reaction mixture as a salt upon addition of a solution of an appropriate acid, preferably chosen among oxalic, fumaric, maleic, methanesulfonic, hydrochloric, hydrobromic, or hydroiodic acid, most preferably oxalic acid, in a suitable solvent (e.g., ethanol, propanol, butanol, methyl t-butyl ether, or acetonitrile).

In another aspect of the invention, the free base of compounds of formula 5 can be obtained from basic, aqueous solutions or suspensions of the corresponding salts upon extractive aqueous work up with an appropriate organic solvent (e.g., methyl t-butyl ether, methyltetrahydrofuran, ethyl acetate, isopropyl acetate, or toluene).

Alternatively, the coupling reaction could be performed by using a salt of compound 7 (e.g., hydrochloride or hydrobromide) and liberating the corresponding base in situ by the action of an appropriate base (e.g., tBuOK or tBuONa) which generates insoluble salts, that can be removed by filtration prior to addition of epoxide 6.

The compound of formula 1 is obtained from compound of formula 5 via a reduction and a mesylation step and cleavage of the protecting group during the reduction step or after the mesylation step.

In a preferred embodiment of the invention the compound of formula 5, or a salt thereof, is:

hydrogenated via hydrogen pressure in a suitable organic solvent, preferably tetrahydrofuran, toluene, alcoholic solvents or mixtures thereof, in the presence of a catalyst tolerating ether bonds, e.g., PtO$_2$, Raney nickel, or Rh/C. The preferred pressure of hydrogen is between 30 psi and 70 psi, preferably 40 psi to 60 psi, in particular 45 psi to 55 psi. The preferred reaction time is between 1 hour and 2 hours, preferably 1.2 hours and 1.8 hours, in particular 1.4 hours to 1.6 hours.

The intermediate product of formula 4

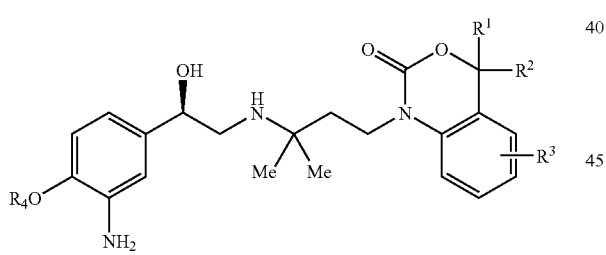

4 or a salt thereof, wherein R$^1$, R$^2$, R$^3$, and R$^4$ are defined as in claims 1 to 3, is obtained by filtering off the catalyst and removing the solvent.

Thereafter the compound of formula 4 is reacted with methansulfonylchloride in the presence of a suitable base, preferably an organic base, e.g., pyridine, picoline, or triethylamine, in an appropriate solvent, e.g., tetrahydrofuran, acetonitrile, or toluene.

The stoichiometric ratio of compound 4 and methansulfonylchloride is preferably between 1:1 and 1:2, particular preferred are ratios from 1:1; 1:1.1; 1:1.2; 1:1.3; 1:1.4; or 1:1.5.

The stoichiometric ratio of compound 4 and pyridine is preferably between 1:1 and 1:4, particular preferred are ratios from 1:1; 1:1.1; 1:1.2; 1:1.3; 1:1.4; 1:1.5; 1:1.6; 1:1.7; 1:1.8; 1:1.9; 1:2; 1:2.1; 1:2.2; 1:2.3; 1:2.4; 1:2.5; 1:2.6; 1:2.7; 1:2.8; 1:2.9; or 1:3.

The preferred reaction time is between 10 hours and 20 hours, more preferably 12 hours and 18 hours.

The reaction is preferably conducted at moderate temperatures, preferably between 10° C. and 30° C., more preferably between 15° C. and 25° C., most preferably at room temperature.

After the reaction, the solvent is removed and the remaining product of formula 2

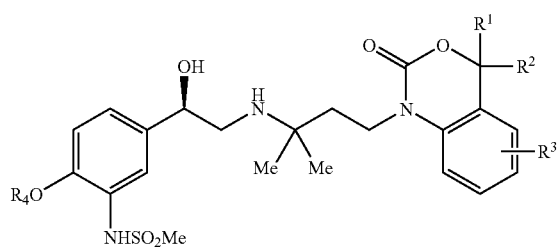

2 wherein R$^1$, R$^2$, R$^3$, and R$^4$ are defined as in claims 1 to 3, is purified as an organic solution (e.g., ethyl acetate, butyl acetate, methyl isobutyl ketone, toluene, or methyl t-butyl ether) via extractive aqueous work up.

A subsequent hydrogenation of 2 in a suitable organic solvent, preferably a mixture of inert solvents, e.g., MeOH, EtOH, toluene, or tetrahydrofuran, and 1-2 equivalents of an acid (e.g., HCl, HBr, or methanesulfonic acid), in the presence of a catalyst, e.g., Pd/C, Pd(OH)$_2$/C, Pd/CaCO$_3$, or Raney nickel, delivers compounds 1. The preferred pressure of hydrogen is between 30 psi and 70 psi, preferably 40 psi to 60 psi, in particular 45 psi to 55 psi. The preferred reaction time is between 0.5 hours and 6 hours, preferably 1 hour and 4 hours, in particular 2 hours to 3 hours.

Products of formula 1

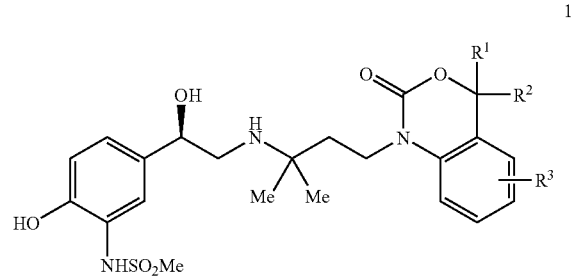

1 or a salt thereof, wherein R$^1$, R$^2$, and R$^3$ are defined as in claims 1 to 3, are obtained by filtering off the catalyst, removing the solvent and crystallizing from a suitable solvent, e.g., acetonitrile, tetrahydrofuran, ethanol, isopropanol, water, or a mixture thereof. Preferably compounds 1 are obtained as a salt, e.g., a hydrochloride or hydrobromide.

In another embodiment of the invention compounds of formula 5, or a salt thereof, are:

hydrogenated via hydrogen pressure in a suitable organic solvent, (e.g., methanol, ethanol, or tetrahydrofuran) in the presence of a catalyst, e.g., Pd/C, Pd(OH)$_2$/C, Pd/CaCO$_3$, Raney nickel. The preferred pressure of hydrogen is between 30 psi and 70 psi, preferably 40 psi to 60 psi, in particular 45 to 55 psi. The preferred reaction time is between 1 hour and 5 hours, preferably 2 hours and 3 hours.

Products of formula 3

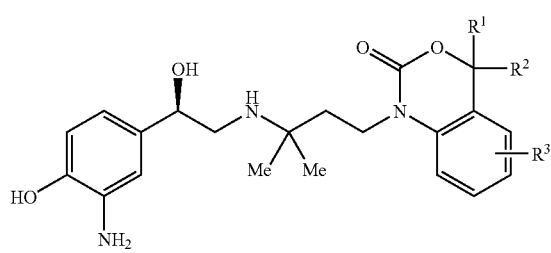

or a salt thereof, wherein $R^1$, $R^2$, and $R^3$ are defined as in claims 1 to 3, are obtained by filtering off the catalyst, removing the solvent and crystallizing from an appropriate solvent (e.g., EtOAc, dichloromethane, toluene, or mixtures thereof).

Thereafter compounds of formula 3 or a salt thereof, are reacted with methansulfonylchloride in the presence of a suitable base, preferably an organic base (e.g., pyridine, picoline, or triethylamine) and a suitable organic solvent (e.g., acetonitrile, tetrahydrofuran, N,N-dimethylformamide, or mixtures thereof).

The stoichiometric ratio of compound 3 and methanesulfonylchloride is preferably between 1:1 and 1:4, particular preferred are ratios from 1:1; 1:1.1; 1:1.2; 1:1.3; 1:1.4; 1:1.5; 1:1.6; 1:1.7; 1:1.8; 1:1.9; 1:2; 1:2.1; 1:2.2; 1:2.3; 1:2.4; 1:2.5; 1:2.6; 1:2.7; 1:2.8; 1:2.9; and 1:3.

The stoichiometric ratio of compound 4 and pyridine is preferably between 1:1 and 1:4, particular preferred are ratios from 1:1; 1:1.1; 1:1.2; 1:1.3; 1:1.4; 1:1.5; 1:1.6; 1:1.7; 1:1.8; 1:1.9; 1:2; 1:2.1; 1:2.2; 1:2.3; 1:2.4; 1:2.5; 1:2.6; 1:2.7; 1:2.8; 1:2.9; 1:3; 1:3.1; 1:3.2; 1:3.3; 1:3.4; 1:3.5; 1:3.6; 1:3.7; 1:3.8; 1:3.9; and 1:4.

The preferred reaction time is between 0.5 hour and 6 hours, more preferably 1 hour and 5 hours, most preferred is a reaction time between 2 hours and 4 hours.

The reaction is preferably conducted at moderate temperatures, preferably between 10° C. and 70° C., more preferably between 20° C. and 45° C.

After the reaction is complete, a reacting solvent (e.g., methanol, ethanol, or aqueous ammonia) is added, the mixture is concentrated and the product of formula 1 is recovered by crystallization from a suitable aqueous solvent mixture (e.g., acetonitrile, tetrahydrofuran, N,N-dimethylformamide, or mixtures thereof) at a controlled pH value.

The preferred pH value of the abovementioned mixture is between 5 and 9, more preferably 6 and 8, particular preferred are pH values of 7.0; 7.1; 7.2; 7.3; 7.5; 7.6; and 7.7.

The product 1 can be further purified via recrystallization as a salt (e.g., hydrochloride, hydrobromide, maleate, fumarate, oxalate, acetate, or methansulfonic acid) from a suitable solvent (e.g., acetonitrile, tetrahydrofuran, ethanol, isopropanol, water, or a mixture thereof) containing the respective acid.

The reduction of the free bases of compounds 5 can also be performed as described above and in the presence of 1 to 1.5 equivalents of an appropriate strong acid, preferably chosen among hydrochloric, methanesulfonic, hydrobromic, hydroiodic, or sulfuric acid, most preferably hydrochloric acid, in solvent suitable for the subsequent mesylation step (e.g., tetrahydrofuran, methyl t-butyl ether, methyltetrahydrofuran, ethyl acetate, isopropylacetate, toluene, or acetonitrile).

The subsequent mesylation step is then performed by filtering off the catalyst, diluting with an appropriate organic solvent (e.g., acetonitrile, tetrahydrofuran, or N,N-dimethylformamide) and adding a suitable base, preferably an organic base (e.g., pyridine, picoline, or triethylamine) followed by addition of methansulfonylchloride.

The stoichiometric ratio of compound 3 and methanesulfonylchloride is preferably between 1:0.9 and 1:1.2, particular preferred are ratios from 1:1; 1:1.05; and 1:1.1.

The stoichiometric ratio of compound 4 and pyridine is preferably between 1:1 and 1:4, particular preferred are ratios from 1:1; 1:1.1; 1:1.2; 1:1.3; 1:1.4; 1:1.5; 1:1.6; 1:1.7; 1:1.8; 1:1.9; 1:2; 1:2.1; 1:2.2; 1:2.3; 1:2.4; 1:2.5; 1:2.6; 1:2.7; 1:2.8; 1:2.9; 1:3; 1:3.1; 1:3.2; 1:3.3; 1:3.4; 1:3.5; 1:3.6; 1:3.7; 1:3.8; 1:3.9; and 1:4.

The preferred reaction time is between 0.5 hour and 6 hours, more preferably 1 hour and 3 hours.

The mesylation reaction is preferably conducted at moderate temperatures, preferably between 0° C. and 45° C.

The work up procedure, the isolation and the purification of compound 1 is performed as described above.

Alternatively, the free base of compounds of formula 3 can be obtained from basic, aqueous solutions or suspensions of the corresponding salts upon extractive aqueous work up with an appropriate organic solvent (e.g., methyl t-butyl ether, methyltetrahydrofuran, ethyl acetate, isopropylacetate, or toluene).

Thereafter, compounds of formula 3, isolated after evaporation of the solvent or solutions of compounds of formula 3, are treated with 1-1.5 equivalents of an appropriate strong acid, preferably chosen among hydrochloric, methanesulfonic, hydrobromic, hydroiodic, or sulfuric acid, most preferably hydrochloric acid, and reacted with methansulfonylchloride in the presence of a suitable base, preferably an organic base (e.g., pyridine, picoline, or triethylamine) and if necessary an additional suitable organic solvent (e.g., acetonitrile, tetrahydrofuran, N,N-dimethylformamide, or mixtures thereof).

The stoichiometric ratio of compound 3 and methanesulfonylchloride is preferably between 1:0.9 and 1:1.2, particular preferred are ratios from 1:1; 1:1.05; and 1:1.1.

The stoichiometric ratio of compound 4 and pyridine is preferably between 1:1 and 1:4, particular preferred are ratios from 1:1; 1:1.1; 1:1.2; 1:1.3; 1:1.4; 1:1.5; 1:1.6; 1:1.7; 1:1.8; 1:1.9; 1:2; 1:2.1; 1:2.2; 1:2.3; 1:2.4; 1:2.5; 1:2.6; 1:2.7; 1:2.8; 1:2.9; 1:3; 1:3.1; 1:3.2; 1:3.3; 1:3.4; 1:3.5; 1:3.6; 1:3.7; 1:3.8; 1:3.9; and 1:4.

The preferred reaction time is between 0.5 hour and 6 hours, more preferably 1 hour and 4 hours.

The reaction is preferably conducted at moderate temperatures, preferably between −5° C. and 45° C., more preferably between 0° C. and 25° C.

The work up procedure, the isolation and the purification of compound 1 is performed as described above.

Furthermore, the above described process is preferred, wherein the compound of formula 6 is obtained by reacting a compound of formula 8

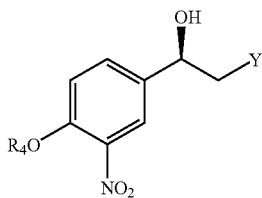

wherein $R^4$ is defined as in claims 1 to 3, and Y is chlorine or a sulfonyloxy based leaving group. Suitable examples include mesyloxy, tosyloxy, benzensulfonyl, or trifluoromethanesulfonyloxy. Particularly preferred is the process wherein Y is chlorine.

Preferred is the process wherein a compound of formula 8 is reacted with a base, preferably an alkali base (e.g., NaOH, KOH, tBuOK, tBuONa, AmONa, or $Na_2CO_3$) in the presence of a suitable solvent. Preferred is an organic solvent, especially preferred are suitable solvents selected form the group consisting of amines, alcohols, ketones, aldehydes, ethers, or aromatic solvents, particularly preferred are N,N-dimethylformamide, ethanol, propanol, and tetrahydrofuran.

The reacted stoichiometric ratio of compounds 8 and the base is preferably between 1:1 and 1:3, particular preferred are ratios from 1:1; 1:1.1; 1:1.2; 1:1.3; 1:1.4; 1:1.5; 1:1.6; 1:1.7; 1:1.8; 1:1.9; and 1:2.

Preferably the base is added to the reaction mixture as a solution, preferably with a concentration between 2 mol/L to 6 mol/L, most preferably between 3 mol/L and 5 mol/L, in particular 3.5 mol/L to 4.5 mol/L.

The reaction is preferably conducted at moderate temperatures, preferably between 10° C. and 30° C., more preferably between 15° C. and 25° C., most preferably at room temperature.

The preferred reaction time is between 10 minutes and 180 minutes, more preferably 20 minutes and 120 minutes, most preferred is a reaction time between 25 minutes and 80 minutes.

After the reaction, water is added preferably together with an organic or inorganic acid (e.g., HCl, $H_2SO_4$, or AcOH) and the product is obtained by filtration.

Compounds 9 can transformed in compounds 8 with the desired configuration at the asymmetric carbon upon stereoselective reduction with borane or a borane complex in the presence of catalytic amounts of a chiral auxiliary. The reduction step is carried out under standard conditions as reviewed in E. J. Corey and C. J. Helal, Angew. Chem. Int. Ed. 1998, 37, 1986-2012. Therefore the above described process is preferred, wherein the compound of formula 8 is obtained by reacting a compound of formula 9

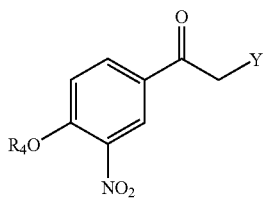

wherein $R^4$ is defined as in claims 1 to 3, and Y is as defined above.

Preferred is the process wherein a compound of formula 9 is reacted with a mixture of a chiral auxiliar and a borane complex in the presence of a suitable solvent. Preferred is an organic solvent, especially preferred are suitable solvents selected form the group consisting of chlorinated solvents, ethers, or aromatic solvents, particularly preferred are toluene and tetrahydrofuran.

The reacted stoichiometric ratio of compounds 9 and the borane is preferably between 1:0.3 and 1:2, particular preferred are ratios from 1:0.5; 1:0.6; 1:0.7; 1:0.8; 1:0.9; 1:1; 1:1.2; and 1:1.3.

The chiral auxiliar is preferably added in an amount of 1%-30% relating to the compound of formula 9, preferred is an amount of 2%-20%, more preferred 3%-10%, most preferred 4%-8%.

With particularly effective chiral auxiliaries, the amount of said auxiliary can be consistently lowered. In these cases, preferred is an amount of 0.05%-2%, more preferred 0.15-1%.

Different chiral auxiliars (or their enantiomers) are disclosed by, for example, E. J. Corey and C. J. Helal, Angew. Chem. Int. Ed. 1998, 37, 1986-2012; Y. Gao at al., WO 9532937 and Tetrahedron Lett. 1994, 35, 6631-6634; U. Kraatz, DE 3609152; S. Itsuno and K. Ito, J. Org. Chem. 1984, 49, 555-557; G. J. Quallich et al., Tetrahedron Lett. 1993, 34, 41454148; S. Itsuno et al., J. Chem. Soc. Perkin Trans I 1983, 1673-1676; or C. H. Senanayake at al., Tetrahedron Lett. 1998, 39, 1705-1708. Preferred is (1S,2S)-(+)-cis-1-amino-2-indanol or one of the following alternatives: (R)-2-methyl-CBS-oxazaborolidine, (R)-(+)-o-tolyl-CBS-oxazaborolidine, (R)-(+)-2-(diphenylhydroxymethyl)pyrrolidine, (1S,2R)-(+)-2-amino-1,2-diphenylethanol, (R)-(−)-2-amino-2-phenylethanol, (R)-(+)-2-amino-3-methyl-1,1-diphenyl-1-butanol, or (1S,2S)-1-amino-1,2,3,4-tetrahydronaphthalen-2-ol.

The generation of the active catalyst may be well performed in situ, as originally described by U. Kraatz in DE 3609152 and by S. Itsuno at al. in J. Chem. Soc. Chem. Commun. 1981, 315-317 and later exemplified by G. J Quallich at al. in Synlett 1993, 929, by combining the chiral auxiliary with excess borane complex in a suitable solvent selected from the group consisting of chlorinated solvents, ethers, or aromatic solvents, particularly preferred are toluene and tetrahydrofuran.

Alternatively, and, for example in the case of (1S,2S)-(+)-cis-1-amino-2-indanol, (R)-(+)-2-(diphenylhydroxymethyl)pyrrolidine, (1S,2R)-(+)-2-amino-1,2-diphenylethanol, (R)-(−)-2-amino-2-phenylethanol, (R)-(+)-2-amino-3-methyl-1,1-diphenyl-1-butanol, and (1S,2S)-1-amino-1,2,3,4-tetrahydronaphthalen-2-ol, the active catalyst is generated by first combining in a suitable solvent the above mentioned chiral auxiliaries with a trialkylborate $B(OR')_3$ ($R'=C_{1-6}$-alkyl) to generate in situ the corresponding 1,3,2,2-alkoxyoxazaborolidines, as for example, described by M. Masui at al. in Synlett 1997, 273-274, followed by addition of a borane complex.

After the formation of the active catalyst, a solution of the compound of general formula 9 in an appropriate solvent as described above is added to the solution of the active catalyst and the borane complex.

In addition other reagents or reagents classes are also known to promote stereoselective reduction of α-halogeno and α-sulfonyloxybenzophenone to the corresponding alcohol. In particular: T. Hamada; T. Torii; K. Izawa; R. Noyori; T. Ikariya, Org. Lett. 2002, 4, 4373-

4376, or J. Chandrasekharan; P. V. Ramachandran; H. C. Brown, *J. Org. Chem.* 1985, 50, 5448-5450.

Suitable, commercially available borane complexes are, for example, $BH_3$-dimethyl sulfite, $BH_3$-THF, $BH_3$-4-methylmorpholine, $BH_3$-N-phenylmorpholine, $BH_3$-N-ethyl-N-isopropylaniline, $BH_3$-N,N-diisopropylethylamine, $BH_3$-triethylamine, or $BH_3$-N,N-diethylaniline, preferred is $BH_3$-N,N-diethylaniline.

The reaction is preferably conducted at temperatures between −5° C. and 80° C., more preferably between 5° C. and 60° C., most preferably between 10° C. and 45° C.

The preferred reaction time is between 30 minutes and 180 minutes, more preferably 40 minutes and 120 minutes, most preferred is a reaction time between 50 minutes and 80 minutes.

If necessary, slower addition of the compound of formula 9 may also be used. The preferred addition time is in these cases between 1.5 hours and 16 hours, more preferably more than 2 hours, most preferred is an addition time longer than 4 hours.

After the reaction, a reacting solvent (e.g., water, methanol, ethanol, or acetone) is added, the reaction mixture concentrated and the product of formula 8 is recovered via treatment with mixtures of aqueous solutions of HCl (preferably a 0.5-1.5 mol/L solution) and organic solvents (e.g., heptane, ethyl acetate, butyl acetate, or methyl t-butyl ether) and recrystallized from a suitable solvent (e.g., ethanol, isopropanol, t-butanol, isopropyl ether, methyl-t-butyl ether, or acetonitrile).

In addition, other reagents or reagents classes can be used for the same transformation. Particularly preferred methods are based on chiral ruthenium complexes (T. Hamada; T. Torii; K. Izawa; R. Noyori; T. Ikariya, *Org. Lett.* 2002, 4, 43734376) or chiral chloroborane (J. Chandrasekharan; P. V. Ramachandran; H. C. Brown, *J. Org. Chem.* 1985, 50, 5448-5450).

In the process described above, compounds 9 are obtained by chlorination or oxidation of the α-position relative to the ketone group of appropriately protected 3-substituted4-hydroxyacetophenones 10, wherein $R^4$ is as defined above. The chlorination may be carried out using conventional chlorinating agents at room or higher temperature. The oxidation can be performed using a variety of agents leading directly to the α-sulfonyloxy-benzophenones (e.g., hydroxy(tosyloxy)iodobenzene, hydroxy(mesyloxy)iodobenzene, J. S. Lodaya and G. F. Koser, *J. Org. Chem.* 1988, 53, 210) or to α-hydroxybenzophenones which are the precursors of a-sulfonyloxybenzophenones (e.g., $Pb(OAc)_4$, phenyliodosobenzene, or $Mn(OAc)_3$). Particularly preferred is the process of chlorinating 10. Therefore the above described process is preferred, wherein the compound of formula 9 is obtained by reacting a compound of formula 10

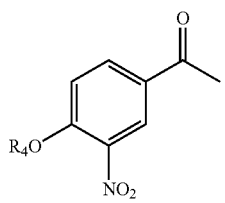

10 wherein $R^4$ is defined as in claims 1 to 3.

Preferred is the process wherein a compound of formula 10 is reacted with a chlorinating agent in the presence of a suitable solvent. Preferred is an organic solvent, especially preferred are suitable solvents selected form the group consisting of alkanes, alcohols, halogenalkanes, ketones, aldehydes, ethers, or nitriles, particularly preferred are heptane, methanol, propanol, tetrahydrofuran, methyl t-butyl ether, diisopropylether, 1,2-dimethoxyethane, dioxane, acetonitrile, dichloromethane, chloroform, alone or mixtures thereof, most preferred are heptane, tetrahydrofuran, methyl t-butyl ether, diisopropylether, 1,2-dimethoxyethane, dioxane, dichloromethane, chloroform, alone or mixtures with methanol thereof, particular preferred are dioxane, acetonitrile, or a mixture of dichloromethane and methanol.

The reacted stoichiometric ratio of compounds 8 and the chlorinating agent is preferably between 1:1 and 1:2, particular preferred are ratios from 1:1; 1:1.1; 1:1.15; 1:1.2; 1:1.25; 1:1.3; 1:1.35; 1:1.4; 1:1.45; and 1:1.5.

The chlorination may be carried out using conventional chlorinating agents. Examples of the chlorinating agent may include, for example, chlorine, seleninyl chloride, hypochlorous acid, N-chlorosuccinimide, cupric chloride, quaternary ammonium polychloride preformed or generated in situ from quaternary ammonium chloride and iodo monochloride, hexachloro-2,4-cyclohexadienone, the complex of 3-chloroperbenzoic acid-hydrogen chloride-N,N-dimethylformamide, or sulfuryl chloride. Specific examples are:

$Cl_2$ AcOH V. Auwers, *Chem. Ber.* 1926, 59, 2899;

$Cl_2$ A;$Cl_3$ $Et_2O/CCl_4$K. Yutaka; S. Takashi; I. Yoshio, *Eur. J Med. Chem. Chim. Ther.* 1981, 16, 355-362;

$BnMe_3ICl_2$ in $ClCH_2CH_2Cl$/MeOH K. Shoji; K. Takaaki; M. Masayuki; F. Shizuo; M. Kimihiro; O. Tsuyoshi, *Synthesis* 1988, 7, 545-546 or in AcOH V. Edwin and W. Jiabing, *Org. Lett.* 2000, 2, 1031-1032;

hexachloro-2,4-cyclohexadienone. G. Alain; L. Marc; G. Jean-Paul, *Synthesis* 1982, 12, 1018-1020;

Preferred chlorinating agents are sulfuryl chloride, N-chlorosuccinimide, or quaternary ammonium polychloride, most preferred is sulfuryl chloride and benzyltrimethylammonium dichloroiodite isolated or generated in situ from benzyltrimethylammonium chloride and iodine monochloride.

The reaction is preferably conducted at moderate temperatures, preferably between 10° C. and 30° C., more preferably between 15° C. and 25° C., most preferably at room temperature.

The preferred reaction time is between 20 minutes and 180 minutes, more preferably 50 minutes and 130 minutes, most preferred is a reaction time between 80 minutes and 100 minutes.

In the case of benzyltrimethylammonium dichloroiodite reaction temperatures higher than 25° C., preferably higher than 50° C. and reaction times between 1 hour and 5 hours, more preferably 2 hours and 4 hours are preferred.

After the reaction, water is added or in the case of benzyltrimethylammonium dichloroiodite an aqueous solution of a reducing agent (such as, for example, sulfite, bisulfite, metabisulfite salts), the product is obtained by filtration and recrystallized from a suitable solvent (e.g., ethyl acetate, isopropyl ether, methyl t-butyl ether, acetonitrile, ethanol, or isopropanol).

USED TERMS AND DEFINITIONS

The term "optionally substituted" refers to nucleus with one or more suitable substituents chosen among: halogen, $C_{1-4}$-alkyl, $C_{1-4}$-alkoxy, and (fused)aryl rings. Preferred substituents are F, Cl, Br, I, Me, Et, OMe, OEt, or O—$^i$Pr.

As used herein "salts" refers to derivatives of the disclosed compounds wherein the parent compound is modified by making acid or base salts thereof. Examples of salts include, but are not limited to, mineral or organic acid salts of basic residues such as amines; alkali or organic salts of acidic residues such as carboxylic acids; and the like. The "pharmaceutically acceptable salts" include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like. The salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred.

The term "—$C_{1-6}$-alkyl" as used herein, either alone or in combination with another substituent, means acyclic, straight or branched chain alkyl substituents containing from one to six carbon atoms and includes, for example, methyl, ethyl, propyl, butyl, pentyl, hexyl, 1-methylethyl, 1-methylpropyl, 2-methylpropyl, or 1,1-dimethylethyl. Possibly conventional abbreviations for these groups are used, e.g., Me, Et, $^i$Pr, or i-Pr.

The term "—$C_{1-6}$-alkylene" as used herein means a divalent alkyl substituent derived by the removal of one hydrogen atom from each end of a saturated straight or branched chain aliphatic hydrocarbon containing from one to six carbon atoms and includes, for example, —$CH_2$—, —$CH_2CH_2$—, —$CH_2CH_2CH_2$—, —$CH_2(CH_2)_2CH_2$—, —$CH_2(CH_2)_2$—, or —$CH_2(CH_2)_4CH_2$—.

EXAMPLES

In the following is a process described suitable for the manufacturing of compounds like:

1a: N-(5-{2-[1,1-Dimethyl-3-(2-oxo4,4-dipropyl-4H-benzo[d][1,3]oxazin-1-yl)propylamino]-1-hydroxyethyl}-2-hydroxyphenyl)methanesulfonamide 1b: N-[5-(2-{1,1-Dimethyl-3-[spiro(cyclohexan-1,4'-2H-3',1'-benzoxazin)-2'-oxo-1-yl]-propylamino}-1-hydroxyethyl)-2-hydroxyphenyl]methanesulfonamide 1c: N-[5-(2-{1,1-Dimethyl-3-[spiro(cyclopropyl-1,4'-2H-3',1'-benzoxazin)-2'-oxo-1-yl]-propylamino}-1-hydroxyethyl)-2-hydroxyphenyl]methanesulfonamide 1d: N-(5-{2-[3-(4,4-Diethyl-2-oxo-4H-benzo[d][1,3]oxazin-1-yl)-1,1-dimethyl-propylamino]-1-hydroxyethyl}-2-hydroxyphenyl)methanesulfonamide 1e: N-(5-{2-[3-(4,4-Diethyl-6-fluoro-2-oxo-4H-benzo[d][1,3]oxazin-1-yl)-1,1-dimethyl-propylamino]-1-hydroxyethyl}-2-hydroxyphenyl)methanesulfonamide 1f: N-(5-{2-[3-(4,4-Diethyl-7-fluoro-2-oxo-4H-benzo[d][1,3]oxazin-1-yl)-1,1-dimethyl-propylamino]-1-hydroxyethyl}-2-hydroxyphenyl)methanesulfonamide 1g: N-(5-{2-[3-(4,4-Diethyl-8-methoxy-2-oxo-4H-benzo[d][1,3]oxazin-1-yl-1,1-dimethyl-propylamino]-1-hydroxyethyl}-2-hydroxyphenyl)methanesulfonamide 1h: N-(5-{2-[3-(4,4-Diethyl-6-methoxy-2-oxo-4H-benzo[d][1,3]oxazin-1-yl)-1,1-dimethyl-propylamino]-1-hydroxyethyl}-2-hydroxyphenyl)methanesulfonamide Therefore $R^1$, $R^2$, and $R^3$ have the meaning corresponding to those groups in examples 1a-1h. For example, if one would like to manufacture compound 1a according to the following examples $R^1$ and $R^2$ would have the meaning of a propyl group and $R^3$ would be H.

1-(4-Benzyloxy-3-nitrophenyl)-2-chloroethanone

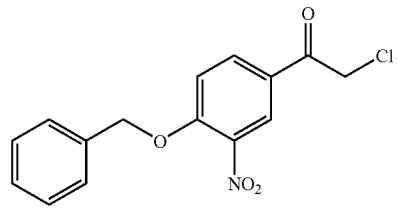

210 g (0.77 mol) of 1-(4-benzyloxy-3-nitrophenyl)ethanone was suspended in dioxane (1.5 L) and treated over 1.5 hours with 68.3 mL (0.84 mol) of sulfuryl chloride. Water (2.4 L) was then slowly added under stirring. The precipitated solid was recovered by filtration, washed with water, and crystallized from ethyl acetate. Yield: 161.0 g (68%); mass spectroscopy: $[M+H]^+$=306; m.p.=141° C.

Alternatively, the title compound can be obtained as follows: 1.36 kg (5.01 mol) of 1-(4-benzyloxy-3-nitrophenyl)ethanone and 2.40 kg of benzyltrimethylammonium chloride (12.53 mol) were dissolved in acetic acid (5.43 L) and acetonitrile (8.2 L) at 65° C. and treated with a 46% aqueous solution of iodine monochloride (4.42 kg, 12.53 mol). The reaction mixture was stirred 2.5 hours at 65° C., then cooled to 5° C. and treated with water (20.4 L) and 5% aqueous sodium bisulfite (24.1 L). The precipitated solid was recovered by filtration, washed with water, and crystallized from ethyl acetate. Yield: 1.21 kg (80.3%); $[M+H]^+$=306.

(R)-1-(4-Benzyloxy-3-nitrophenyl)-2-chloroethanol

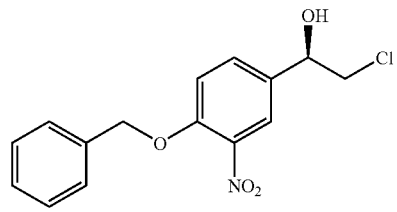

Example A 4.5 g (30.0 mmol) of (1S,2S)-(+)-cis-1-amino-2-indanol was dissolved in dry THF (110 mL). The solution was cooled to 3° C. and a solution of 51.4 g (0.31 mol) of borane-N,N- diethylaniline complex in dry THF (0.2 L) was added. After 20 minutes, a solution of 183.4 g (0.60 mol) of 1-(4-benzyloxy-3-nitrophenyl)-2-chloroethanone in dry THF (2.2 L) was slowly added, keeping the temperature below 23° C. After one hour at this temperature, the reaction mixture was slowly treated with MeOH (0.22 L) and concentrated. The residual was treated with n-heptane (0.6 L) and HCl (1 mol/L, 50 mL) and the mixture cooled to 2° C. The precipitated product was collected by filtration and crystallized from isopropyl alcohol (0.66 L). Yield: 154 g (83.4%); mass spectroscopy: [M+H]$^+$=308; m.p.=94° C.; e.e. 99.6%.

Example B

A 1 M solution of (R)-2-methyl-CBS-oxazaborolidine in toluene (0.16 mL, 0.16 mmol) and 3.0 mL (16.87 mmol) of borane-N,N-diethylaniline complex were dissolved at room temperature in 7 mL of THF (water content <0.02%). After 15 minutes, the solution was set to +35° C. and a solution of 5.0 g (16.36 mmol) of 1-(4-benzyloxy-3-nitrophenyl)-2-chloroethanone in 50 mL of THF (water content <0.02%) was added over 5 hours at this temperature. At the end of the addition, the solution was slowly treated with MeOH (10 mL) and eventually concentrated. The residual was dissolved in methyl t-butyl ether (50 mL) and the solution washed with HCl (1 mol/L, 17 mL) and brine (10 mL). The organic phase was separated, dried over Na$_2$SO$_4$, and evaporated. The resulting product was crystallized from isopropyl alcohol (17 mL). Yield: 3.6 g (72.0%); mass spectroscopy: [M+H]$^+$=308; e.e. 100%.

Example C

A 1 M solution of (R)-2-methyl-CBS-oxazaborolidine in toluene (0.017 mL, 0.017 mmol) and 3.0 mL (16.87 mmol) of borane-N,N-diethylaniline complex were dissolved at room temperature in 7 mL of THF (water content <0.02%). The solution was stirred for 15 minutes at this temperature and set to 25° C. A solution of 5.0 g (16.36 mmol) of 1-(4-benzyloxy-3-nitrophenyl)-2-chloroethanone in 50 mL of THF (water content <0.02%) was is added over 5 hours at this temperature. At the end of the addition, the solution was stirred one additional hour at this temperature and then slowly treated with MeOH (10 mL) and eventually concentrated. The residual was dissolved in methyl t-butyl ether (50 mL) and the solution washed with HCl (1 mol/L, 17 mL) and brine (10 mL). The organic phase was separated, dried over Na$_2$SO$_4$ and evaporated. The resulting product was crystallized from isopropyl alcohol (17 mL). Yield: 3.6 g (71.5%); mass spectroscopy: [M+H]$^+$=308; e.e. 99.7%

Example D (R)-(−)-2-amino-2-phenylethanol, 112 mg (0.82 mmol) and 3.0 mL (16.87 mmol) of borane-N,N-diethylaniline complex were dissolved at room temperature in 7 mL of THF (water content <0.02%). The solution was stirred 1 hour at this temperature and set to 35° C. A solution of 5.0 g (16.36 mmol) of 1-(4-benzyloxy-3-nitrophenyl)-2-chloroethanone in 50 mL of THF (water content <0.02%) was added over 6 hours at this temperature. At the end of the addition, the solution was slowly treated with MeOH (10 mL) and eventually concentrated. The residual was dissolved in methyl t-butyl ether (50 mL) and the solution washed with HCl (1 mol/L, 17 mL) and brine (10 mL). The organic phase was separated, dried over Na$_2$SO$_4$ and evaporated. The resulting product was crystallized from isopropyl alcohol (17 mL). Yield: 3.5 g (70.0%); mass spectroscopy: [M+H]$^+$=308; e.e. 97.6%.

Example E (1S,2R)-(+)-2-amino-1,2-diphenylethanol (174 mg, 0.82 mmol), and 3.0 mL (16.87 mmol) of borane-N,N-diethylaniline complex were sequentially dissolved at room temperature in 7 mL of THF (water content <0.02%). The solution was stirred for 45 minutes at this temperature and set to 35° C. A solution of 5.0 g (16.36 mmol) of 1-(4-benzyloxy-3-nitrophenyl)-2-chloroethanone in 50 mL of THF (water content <0.02%) was added over 6 hours at this temperature. At the end of the addition, the solution was slowly treated with MeOH (10 mL) and eventually concentrated. The residual was dissolved in methyl t-butyl ether (50 mL) and the solution washed with HCl (1 mol/L, 17 mL) and brine (10 mL). The organic phase was separated, dried over Na$_2$SO$_4$, and evaporated. The resulting product was crystallized from isopropyl alcohol (17 mL). Yield: 3.7 g (74.0%); mass spectroscopy: [M+H]$^+$=308; e.e. 99.2%.

Example F (R)-(+)-2-(diphenylhydroxymethyl)pyrrolidine (42 mg, 0.17 mmol) and 3.0 mL (16.87 mmol) of borane-N,N-diethylaniline complex were dissolved at room temperature in 7 mL of THF (water content <0.02%). The solution was stirred 16 hours at this temperature then set to 25° C. A solution of 5.0 g (16.36 mmol) of 1-(4-benzyloxy-3-nitrophenyl)-2-chloroethanone in 50 mL of THF (water content <0.02%) was added over 5 hours at this temperature. At the end of the addition, the solution was slowly treated with MeOH (10 mL) and eventually concentrated. The residual was dissolved in methyl t-butyl ether (50 mL) and the solution washed with HCl (1 mol/L, 17 mL) and brine (17 mL). The organic phase was separated, dried over Na$_2$SO$_4$, and evaporated. The resulting product was crystallized from isopropyl alcohol (17 mL). Yield: 3.7 g (74.0%); mass spectroscopy: [M+H]$^+$=308; e.e. 100%.

Example G (1S,2S)-(+)-cis-1-amino-2-indanol (76 mg, 0.51 mmol) and trimethyl borate (0.070 mL, 0.63 mmol) were sequentially dissolved at 25° C. in 7 mL of THF (water content <0.02%). After 1 hour, 3.0 mL (16.87 mmol) of borane-N,N-diethylaniline complex was added. The solution was stirred for 15 minutes at this temperature then set to +35° C. and a solution of 5.0 g (16.36 mmol) of 1-(4-benzyloxy-3-nitrophenyl)-2-chloroethanone in 50 mL of THF (water content <0.02%) was added over 5 hours at this temperature. At the end of the addition, the solution was slowly treated with MeOH (10 mL) and eventually concentrated. The residual was dissolved in methyl t-butyl ether (50 mL) and the solution washed with HCl (1 mol/L, 17 mL) and brine (17 mL). The organic phase was separated, dried over Na$_2$SO$_4$, and evaporated. The resulting product was crystallized from isopropyl alcohol (17 mL). Yield: 3.7 g (74.0%); mass spectroscopy: [M+H]$^+$=308; e.e. 99.6%.

(R)-2-(4-Benzyloxy-3-nitrophenyl)oxirane

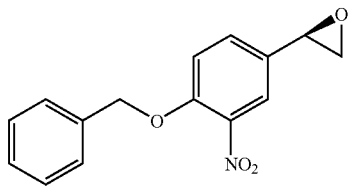

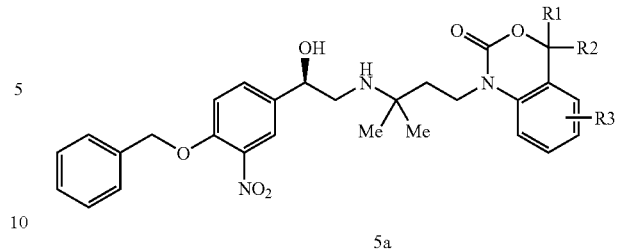

5a 151.8 g (0.49 mol) of 1-(4-benzyloxy-3-nitrophenyl)-2-chloroethanol was dissolved in THF (0.75 L) and treated dropwise with NaOH (4 mol/L, 182 mL, 0.73 mol). After 1 hour, AcOH (30 mL) was added followed by water (2.5 L). The mixture was cooled and the precipitated product was recovered by filtration and dried under vacuum at 65° C. Yield: 133.0 g (99.3%); mass spectroscopy: $[M+H]^+ = 272$; m.p.=66° C.; e.e. 99.5%.

Ring Opening of
2-(4-benzyloxy-3-nitrophenyl)oxirane by neopentyl
benzoxazinone-based amines

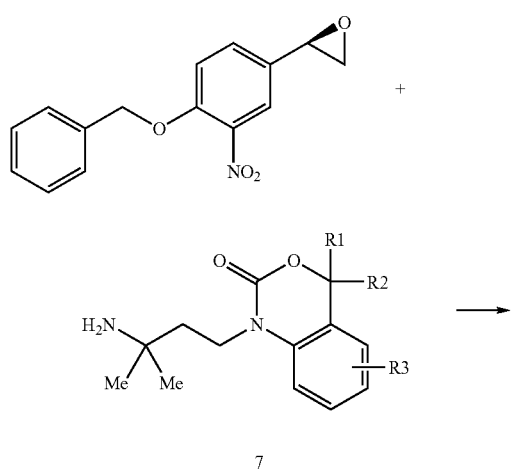

A solution of 2-(4-benzyloxy-3-nitrophenyl)oxirane (1.58 kg, 5.82 mol) in tetrahydrofuran (4.16 L) and n-BuOH (4.00 L) was added to a refluxing solution of the amine 7 (6.12 mol) in n-BuOH (19.50 L) over 5 hours with continuous removal of solvent. At the end of the addition, a total of 19 L of solvent were collected. The solution was refluxed for additional 2 hours, then cooled to 94° C. and treated with a solution of oxalic acid (0.525 kg, 5.83 mol) in EtOH 90% (8.90 L). Upon cooling to room temperature, the oxalate of 5a crystallized from the reaction mixture. This was recovered by filtration, washed with EtOH/TBME (2×1 L), and dried under vacuum at 60° C. Yield: 75.0%.

Alternatively, compounds 5a could be prepared as follows: the chloridrate of the amine 7 (148.0 mmol) was added to a solution of potassium tert-butylate (17.6 g, 154.0 mmol) in n-BuOH (0.5 L). After one hour the insolubles were filtered off and washed with n-BuOH (0.06 L) and the resulting clear solution treated with 2-(4-benzyloxy-3-nitrophenyl)oxirane (40 g, 140.0 mmol). The reaction mixture was refluxed for 6 hours and then treated with a solution of oxalic acid (12.7 g, 141.1 mmol) in EtOH 90% (0.2 L). Upon cooling to room temperature the oxalate of 5a crystallized from the reaction mixture. This was recovered by filtration, washed with EtOH/TBME (2×100 mL) and dried under vacuum at 45° C. Yield: 64.6%.

Compounds 5a as free bases could be recovered after basic work up and extraction with the appropriate solvent as follows:

The oxalate of compound 5a (80.0 mmol) was suspended in water (0.3 L) and methyl t-butyl ether (0.25 L), 32% aqueous ammonia was added (30 mL) and the organic phase was separated. The aqueous phase was extracted with methyl t-butyl ether (2×0.1 L) and the combined extracts were washed with water (0.1 L) and brine (0.1 L) and dried ($Na_2SO_4$). Evaporation of the solvent gave compound 5a as the free base.

Reduction of the Nitro Function

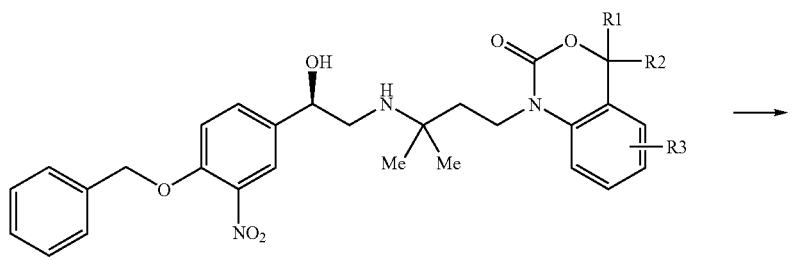

5a

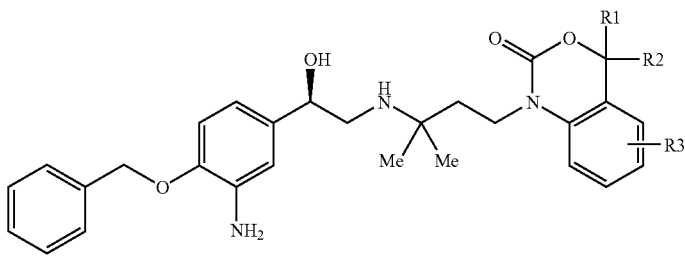

4a

The nitro compound 5a (free base, 13.0 mmol) was dissolved in THF (70 mL)/toluene (70 mL) and hydrogenated at 50 psi in the presence of PtO$_2$ (3.5 mmol). After 1.5 hours, the catalyst was filtered off and the solvents were removed under reduced pressure to afford the anilino compound 4a. Yield: 96.0%.

Mesylation of the Anilino Function

A solution of compound 4a (148.5 mmol) in THF (0.8 L) was treated with pyridine (24.0 mL, 298.0 mmol) followed by neat methansulfonylchloride (12.0 mL, 155.0 mmol). After 16 hours, the reaction mixture was concentrated under reduced pressure and the residual material partitioned between ethyl acetate (1 L) and 1% aq. NaHCO$_3$ (0.6 L). The organic phase was washed sequentially with water (0.5 L) and brine (0.1 L). The organic phase was dried over sodium sulfate and the solvent evaporated to afford crude sulfonamide 2a. Yield: 93.1%.

Removal of Benzyl Protecting Group

Crude sulfonamide 2a (83.25 mmol) obtained as described above was dissolved in a mixture of MeOH (0.5 L) and 37% aq. HCl (7.9 mL) and hydrogenated at 50 psi in the presence of Pd/C 10% (5.0 g). After 2 hours, the catalyst was filtered off, the solvent was removed under reduced pressure, and the residual crystallized from acetonitrile (580 mL) and water (1 mL) to give the hydrochloride of compound 1. Yield: 36.2%.

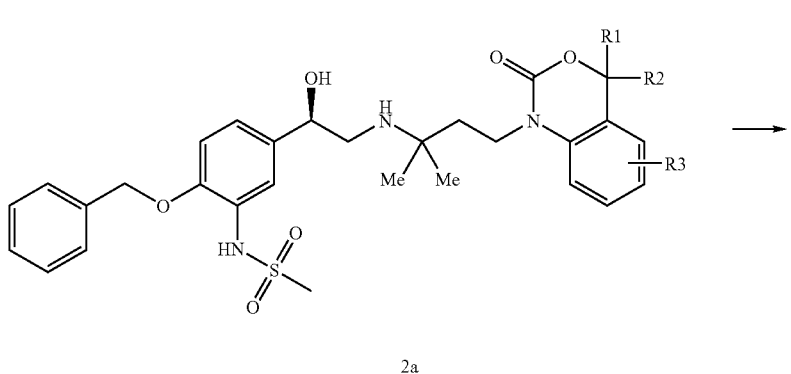

2a

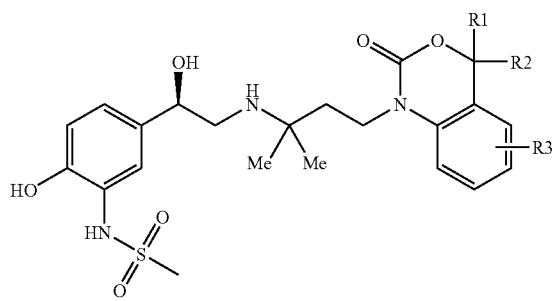

1

Alternatively, is possible to prepare compounds 1 according to the following procedure:

Reduction of the Nitro Function and Removal of the Benzyl Protecting Group

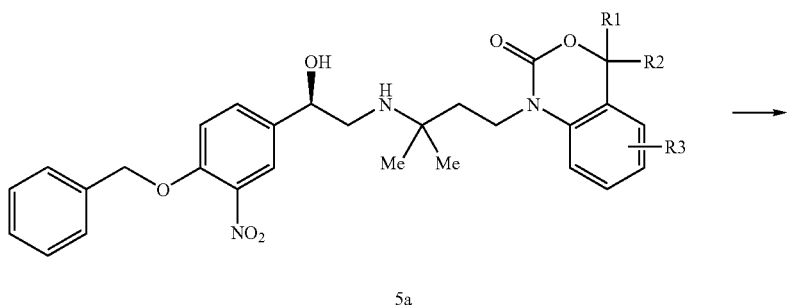

5a

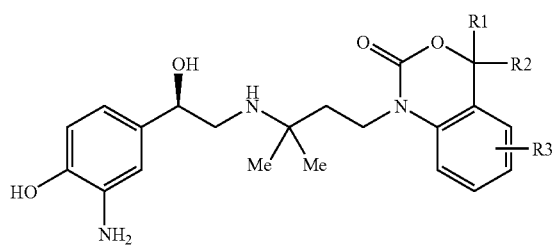

3

The oxalate of nitro compound 5a (1.11 mol) was suspended in MeOH (7.24 L) and hydrogenated at 50 psi in the presence of Pd/C 10% (36.2 g). After 2.5 hours, the catalyst was filtered off and the solvent was removed under reduced pressure and the residue triturated in hot EtOAc (4.0 L) to give the oxalate of compound 3. Yield: 99.1%.

If desired, compounds 3 as free bases could be recovered after basic work up and extraction with the appropriate solvent as follows:

The oxalate of compound 3 (1.69 mol) was dissolved in water (4.0 L) under an argon atmosphere. The solution was partitioned between cold water (7.2 L) and ethyl acetate (7.2 L) and 32% aqueous ammonia was added (0.61 L). The organic phase was separated, washed with water (5.4 L) and brine (0.75 L) and filtered over $Na_2SO_4$ (1.6 kg) and charcoal (0.2 kg). Evaporation of the solvent gave compound 3 as the free base.

Mesylation of the Anilino Function

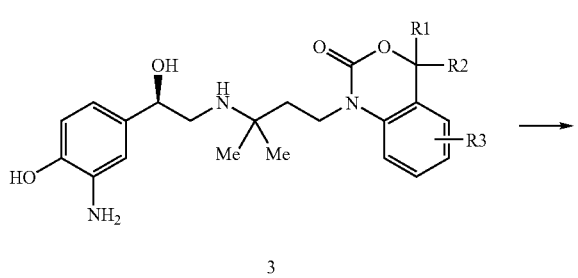

3

-continued

1

The oxalate of compound 3 (2.07 mol) was dissolved in a mixture of acetonitrile (7.70 L) and tetrahydrofuran (7.70 L) and treated with pyridine (0.54 L, 6.62 mol). The reaction mixture was treated over one hour with a solution of methanesulfonyl chloride (0.32 L, 4.14 mol) in acetonitrile (1.65 L) keeping the temperature between 25 and 33° C. After a total time of 3 hours MeOH (0.2 L) was added and the reaction mixture concentrated. Water (5.5 L) and acetonitrile (0.55 L) were added and the pH set to 7.3 with saturated aqueous $NaHCO_3$ (10.0 L) while the product crystallized. The precipitated solid was collected by filtration, washed with water (2×1.5 L) and TBME (3×1.0 L) and dried at 60° C. to give 1 as the free base. This material was transformed into the corresponding hydrochloride upon crystallization from a mixture of acetonitrile (10.7 L) and 37% aq. HCl (165.6 mL). Yield: 75.7%.

Alternatively, compounds 1 can be obtained from the free base of compound 3 as follows: The free base of compound 3 (1.69 mol) was dissolved in a mixture of tetrahydrofuran (7.5 L) and acetonitrile (7.5 L) at 50° C. The solution was cooled to 5° C. and concentrated hydrochloric acid (139 mL, 1.69 mol) was added followed by pyridine (287 mL, 3.55 mol). At 3° C. a solution of methanesulfonyl chloride (131 mL, 1.69 mol) in acetonitrile (0.75 L) was added over 20 minutes. After an additional 2 hours, MeOH (205 mL) was added, the temperature was set to 30° C. and the reaction mixture concentrated. Water (4.25 L) and acetonitrile (1.5 L) were then added to the residue followed by saturated aqueous NaHCO$_3$ (2.3 L). Some crystals of 1 were added followed by additional saturated aqueous NaHCO$_3$ (2.3 L) while the product crystallized. The precipitated solid was recovered by filtration, washed with water (2×1.7 L) and TBME (2×2.5 L) and dried at 60° C. to give 1 as the free base. Yield: 87.4%.

This material was transformed into the corresponding hydrochloride by suspending it in acetonitrile (9.3 L) and pyridine (11.8 g, 0.147 mol), and treating the mixture with concentrated hydrochloric acid (120 mL, 1.45 mol) in acetonitrile (1.22 L). The mixture was heated to 67° C. and the obtained solution filtered. Upon cooling, the hydrochloride of 1 crystallized. This was recovered by filtration, washed with acetonitrile (2×1.6 L) and methyl t-butyl ether (2×1.6 L) and dried at 50° C. Yield: 77.3%.

Alternatively, compounds 1 can be obtained from the free base of compound 5a as follows: The free base of compound 5a (67.1 mmol) was dissolved in tetrahydrofuran (0.3 L), concentrated hydrochloric acid (5.6 mL, 67.1 mmol) was added and the solution hydrogenated at 50 psi in the presence of Pd/C 10% (3.8 g). After 2.5 hours, the catalyst was filtered off and the solution diluted with acetonitrile (0.3 L). The temperature was set to 30° C. and pyridine (12.5 mL, 154.1 mmol) was added followed by addition of a solution of methanesulfonyl chloride (5.2 mL, 67.0 mol) in acetonitrile (20 mL) over 20 minutes. After an additional 45 minutes, MeOH (8 mL) was added and the reaction mixture concentrated. Water (170 mL) and acetonitrile (60 L) were added followed by saturated aqueous NaHCO$_3$ (100 mL). Some crystals of 1 were added followed by additional saturated aqueous NaHCO$_3$ (120 mL) while the product crystallized. The precipitated solid was recovered by filtration, washed with water (2×80 mL) and TBME (2×80 mL). If desired, compound 1 could be further purified by suspending it in hot ethyl acetate (350 mL)/isopropanol (50 mL) mixtures. The suspension was cooled and the solid was collected by filtration, washed with ethyl acetate (2×50 mL) and dried at 50° C. to give 1 as the free base. Yield: 71.5%. The free base of 1 could be transformed into the corresponding hydrochloride as described above.

We claim:

1. A process for making a compound of formula 1

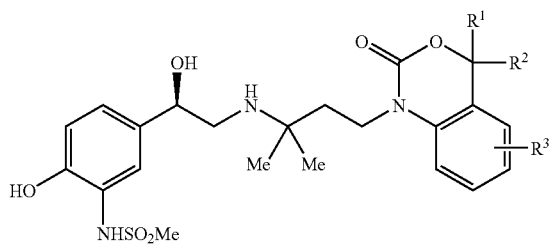

or a salt thereof, wherein:

$R^1$ and $R^2$ are each independently H, halogen, or $C_{1-4}$-alkyl, or $R^1$ and $R^2$ together are $C_{1-6}$-alkylene; and $R^3$ is H, halogen, OH, $C_{1-4}$-alkyl, or O—$C_{1-4}$-alkyl, the process comprising:

(a) reacting a compound of formula 6

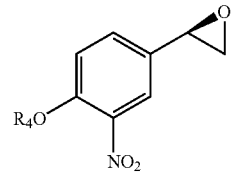

wherein $R^4$ is benzyl, diphenylmethyl, or trityl, each optionally substituted at, if available, an aryl group or an aliphatic carbon atom, with a compound of formula 7

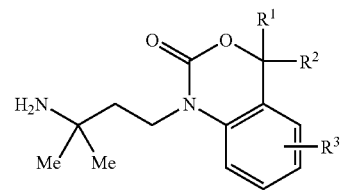

or a salt thereof, to obtain a compound of formula 5, or a salt thereof

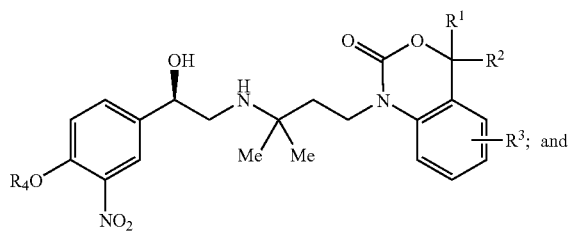

(b) reducing the nitro group of the compound of formula 5 to an amine group and mesylating this amine group and cleaving the $R^4$ protecting group during the reduction step or after the mesylation step to obtain the compound of formula 1.

2. The process according to claim 1, wherein:

$R^1$ and $R^2$ each independently H, F, Cl, methyl, ethyl, propyl, or butyl, or $R^1$ and $R^2$ together are ethylene, propylene, butylene, or pentylene;

$R^3$ is H, F, Cl, OH, methyl, ethyl, methoxy or ethoxy; and $R^4$ is benzyl or diphenylmethyl, each optionally substituted at, if available, an aryl group or an aliphatic carbon atom with F, Cl, Br, Me, Et, OMe, OEt, or O—$^i$Pr.

3. The process according to claim 1, wherein:

$R^1$ and $R^2$ are each independently H, methyl, ethyl, or propyl, or $R^1$ and $R^2$ together are ethylene, propylene, butylene, or pentylene;

$R^3$ is H, F, OH, methyl, or methoxy; and $R^4$ is benzyl optionally substituted at the aryl group or the aliphatic carbon atom with F, Cl, Br, Me, Et, OMe, OEt, or O—$^i$Pr.

4. The process according to one of claims 1 to 3, wherein the compound of formula 6 is obtained by reducing a compound of formula 8

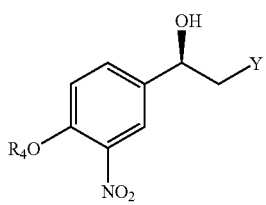

8 wherein $R^4$ is benzyl, diphenylmethyl, or trityl, each optionally substituted at, if available, an aryl group or an aliphatic carbon atom, and Y is chlorine or a sulfonyloxy based leaving group.

5. The process according to one of claims 1 to 3, wherein the compound of formula 6 is obtained by reducing a compound of formula 8

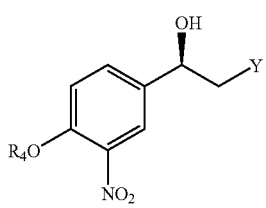

8 wherein $R^4$ is benzyl or diphenylmethyl, each optionally substituted at, if available, an aryl group or an aliphatic carbon atom with F, Cl, Br, Me, Et, OMe, OEt, or O—$^i$Pr, and Y is chlorine or a sulfonyloxy based leaving group.

6. The process according to one of claims 1 to 3, wherein the compound of formula 6 is obtained by reducing a compound of formula 8

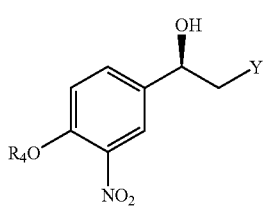

8 wherein $R^4$ is benzyl optionally substituted at the aryl group or the aliphatic carbon atom with F, Cl, Br, Me, Et, OMe, OEt, or O—$^i$Pr, and Y is chlorine or a sulfonyloxy based leaving group.

7. The process according to claim 4, wherein Y is chlorine.
8. The process according to claim 5, wherein Y is chlorine.
9. The process according to claim 6, wherein Y is chlorine.

10. The process according to claim 4, wherein the compound of formula 8 is obtained by reducing a compound of formula 9

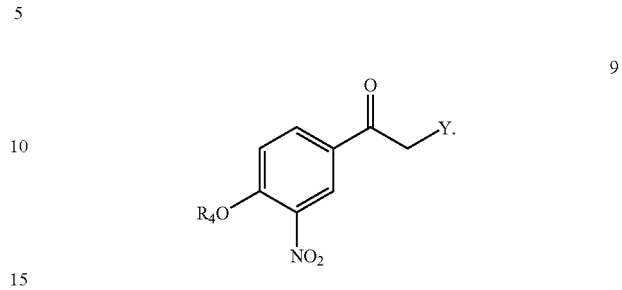

9

11. The process according to claim 5, wherein the compound of formula 8 is obtained by reducing a compound of formula 9

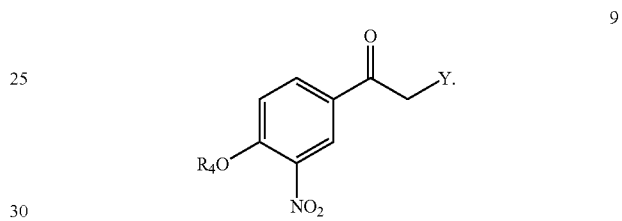

9

12. The process according to claim 6, wherein the compound of formula 8 is obtained by reducing a compound of formula 9

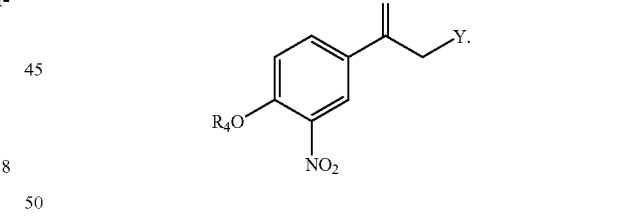

9

13. The process according to claim 7, wherein the compound of formula 8 is obtained by reducing a compound of formula 9

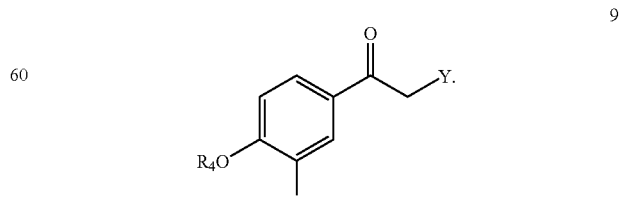

9

14. The process according to claim 8, wherein the compound of formula 8 is obtained by reducing a compound of formula 9

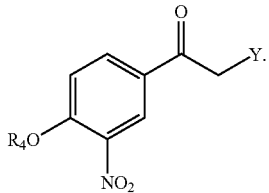
9

15. The process according to claim 9, wherein the compound of formula 8 is obtained by reducing a compound of formula 9

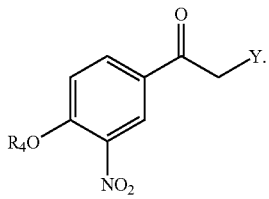
9

16. The process according to claim 10, wherein the compound of formula 9 is obtained by reducing a compound of formula 10

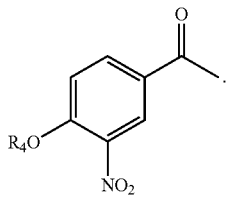
10

17. The process according to claim 11, wherein the compound of formula 9 is obtained by reducing a compound of formula 10

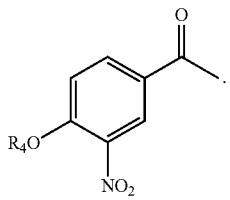
10

18. The process according to claim 12, wherein the compound of formula 9 is obtained by reducing a compound of formula 10

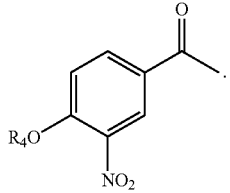
10

19. The process according to claim 13, wherein the compound of formula 9 is obtained by reducing a compound of formula 10

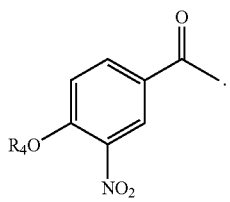
10

20. The process according to claim 14, wherein the compound of formula 9 is obtained by reducing a compound of formula 10

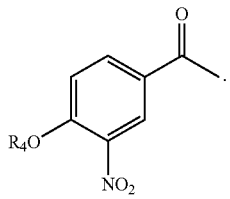
10

21. The process according to claim 15, wherein the compound of formula 9 is obtained by reducing a compound of formula 10

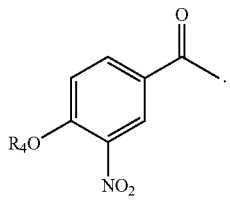
10

* * * * *